United States Patent
Pletcher et al.

(10) Patent No.: US 6,432,349 B1
(45) Date of Patent: Aug. 13, 2002

(54) PROCESS OF MAKING AN ARTICULATING BEARING SURFACE

(75) Inventors: Dirk Pletcher, Walkerton; Steve T. Lin, Fort Wayne, both of IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 09/342,324

(22) Filed: Jun. 29, 1999

(51) Int. Cl.⁷ .......................... B29C 35/08; B29C 37/02; B29C 43/02

(52) U.S. Cl. .......................... 264/479; 264/39; 264/162; 264/322; 264/488; 264/494

(58) Field of Search .......................... 264/39, 162, 320, 264/322, 479, 488, 494

(56) References Cited

U.S. PATENT DOCUMENTS

| | | | |
|---|---|---|---|
| 3,297,641 A | | 1/1967 | Werber et al. |
| 3,352,818 A | | 11/1967 | Meyer et al. |
| 3,758,273 A | | 9/1973 | Johnston et al. |
| 5,037,928 A | | 8/1991 | Li et al. |
| 5,160,464 A | | 11/1992 | Ward et al. |
| 5,414,049 A | | 5/1995 | Sun et al. |
| 5,449,745 A | | 9/1995 | Sun et al. |
| 5,466,530 A | | 11/1995 | England et al. |
| 5,543,471 A | | 8/1996 | Sun et al. |
| 5,824,411 A | * | 10/1998 | Shalaby et al. ......... 264/322 X |
| 5,879,400 A | | 3/1999 | Merrill et al. |
| 6,017,975 A | | 1/2000 | Saum et al. |
| 6,143,232 A | * | 11/2000 | Rohr ...................... 264/320 X |
| 6,228,900 B1 | | 5/2001 | Shen et al. |

FOREIGN PATENT DOCUMENTS

| | | |
|---|---|---|
| EP | 722973 A1 | 7/1986 |
| WO | WO98/01085 | 1/1998 |

OTHER PUBLICATIONS

Super Low Wear Cross–Linked UHMWPE by Heavy High––Dose Gamma Radiation Oonishi, H., Kuno, M., Idada, Y., Fujisawa, A., and Masuda, S. 1996 WPOA 2$^{nd}$ Congress of Hip Section.

Journal of Polymer Science, Part B, Polymer Letters Editorial Board: R.M. Fuoss, J.J. Hermans, H. Mark, H.W. Melville, C.G. Overberger, G. Smets vol. 1, No., Feb. 1963.

The Improvement of Polyethylene Prostheses Through Radiation Crosslinking T.A. du Plessis, C. J. Grobbelaar, and F. Marais Radiat. Phys. Chem. 1977, vol. 9, pp. 647–652.

The Friction and Wear Behavior of Irradiated Very High Lecular Weight Polyethylene C. Shen and J.H. Dumbleton Wear, (1974) pp. 349–364.

Crystalline and Supermolecular Structures in Linear Polyethylene Irradiated with Fast Electrons G. Gielenz and B. J. Jungnickel Colloid & Polymer Science 260, pp. 742–753 (1982).

Improved Mechanical Behaviour in Ultra–High Modulus Polyethylenes by Controlled Cross–Linking D. W. Woods, W. K. Busfield and I.M. Ward Plastics and Rubber Processing and Applications 5 (1985) pp. 157–164.

(List continued on next page.)

Primary Examiner—Leo B. Tentoni
(74) Attorney, Agent, or Firm—Jacque R. Wilson

(57) ABSTRACT

A method of manufacturing an articulating bearing surface for use in an orthopaedic implant is disclosed. A block of ultra-high molecular weight polyethylene is irradiated with sufficient radiation energy to crosslink at least a portion of the ultra-high molecular weight polyethylene. The irradiated block is placed within a reforming apparatus having a complimentary articulating bearing surface. The block is heated and pressed against the complimentary articulating bearing surface, thereby forming the articulating bearing surface.

14 Claims, 3 Drawing Sheets

OTHER PUBLICATIONS

Irradiation of Ultrahigh–Molecular–Weight Polyethylene A. Shinde and R. Salovey Journal of Polymer Science: Polymer Physics Edition, vol. 23, 1681–1689 (1985).

Ionizing Irradiation for Sterilization and Modification of High Molecular Weight Polyethylenes Robert M. Streicher Plastics and Rubber Processing and Applications vol. 10, No. 4, 1988.

Influence of Ionizing Irradiation in Air and Nitrogen for Sterilization of Surgical Grade Polyethylene for Implants R. M. Streicher Radiat. Phys. Chem, vol. 31, Nos 4–6, pp. 693–698, 1988.

Improvement of Polyethylene by Irradiation in Artificial Joints H. Oonishi, Y. Takayama, and E. Tsuri Radiat. Phys. Chem. vol. 39, No. 6, pp. 495–504, 1992.

The Radiation Chemistry of Polyethylene. IX. Temperature Coefficient of Cross–Linking and Other Effects H. Y. Kang, O. Saito, and M. Dole Journal of the American Chemical Society, 89:9, Apr. 26, 1967.

The Radiation Improvement of Polyethylene Prostheses, A Preliminary Study C. J. Grobbelaar, T. A. Du Plessis, F. Marais The Journal of Bone and Joint Surgery 60–B, No. 3, Aug. 1978, pp. 370–374.

The Effects of Radiation Sterilization on the Properties of Ultrahigh Molecular Weight Polyethylene H. J. Nusbaum and R. M. Rose Journal of Biomedical Materials Research, vol. 13, pp. 557–576 (1979).

Crystalline and Supermolecular Structures in Linear Polyethylene Irradiated with Fast Electrons G. Gielenz and B. J. Jungnickel. Colloid & Polymer Science 260, pp. 742–753 (1982).

Radiation Sterilization and the Wear Rate of Polyethylene R. M. Rose, E. V. Goldfarb, E. Ellis, and A. N. Crugnola Journal of Orthopaedic Research, pp. 393–400, 1984 Orthopaedic Research Society.

Cross–Linking of Ultra–High Molecular Weight Polyethylene in the melt by means of Electron Beam Irradiation D. J. Dijkstra, W. Hoogsteen, and A. J. Pennings. Polymers, 1989; vol. 30, Mayo.

Improvement of Polyethylene by Irradiation in Artificial Joints H. Oonishi, Y. Takayama, and E. Tsuji, Radiat. Phys. Chem. vol. 39, No. 6, pp. 495–504 1992.

Effect of $\tau$ Irradiation on the Friction and Wear of Ultrahigh Molecular Weight Polyethylene William R. Jones, Jr., and William F. Hady, Wear, 70 (1981) 77–92.

* cited by examiner

PROCESS OF MAKING AN ARTICULATING BEARING SURFACE

BACKGROUND OF THE INVENTION

1. Field of the Invention

The present invention relates to orthopaedic implants, and more particularly, to articulating bearing surfaces for orthopaedic implants.

2. Description of the Related Art

Orthopaedic implants used to reconstruct a joint of a patient typically include two implant halves with each implant half defining an articulating bearing surface. For example, an orthopaedic knee implant includes a proximal component which is placed within the femur and a distal component which is placed within the tibia. The proximal component typically includes a metallic articulating bearing surface which pivots on a non-metallic articulating bearing surface defined by the tibial knee component. The non-metallic bearing surface may be formed from a block of ultra-high molecular weight polyethylene (UHMWPE), which is machined to define the articulating bearing surface. The non-metallic bearing surface is attached to and carried by a tibial tray, which in turn is affixed to a stem inserted within the intramedullary canal of the tibia.

SUMMARY OF THE INVENTION

The present invention provides a method of manufacturing an articulating bearing surface for use in an orthopaedic implant, wherein a crosslinked UHMWPE block is near-net shaped and reformed under heat and pressure to define a net shaped articulating bearing surface.

The invention comprises, in one form thereof, a method of manufacturing an articulating bearing surface for use in an orthopaedic implant. A block of ultra-high molecular weight polyethylene is irradiated with sufficient radiation energy to crosslink at least a portion of the ultra-high molecular weight polyethylene. The irradiated block is placed within a reforming apparatus having a complimentary articulating bearing surface. The block is heated and pressed against the complimentary articulating bearing surface, thereby forming the articulating bearing surface.

An advantage of the present invention is that a net shaped articulating bearing surface with improved surface finish, wear resistance, and abrasions resistance is provided.

Another advantage is that additional machining is not required to define the articulating bearing surface after the reforming of the articulating bearing surface under heat and pressure.

BRIEF DESCRIPTION OF THE DRAWINGS

The above-mentioned and other features and advantages of this invention, and the manner of attaining them, will become more apparent, and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
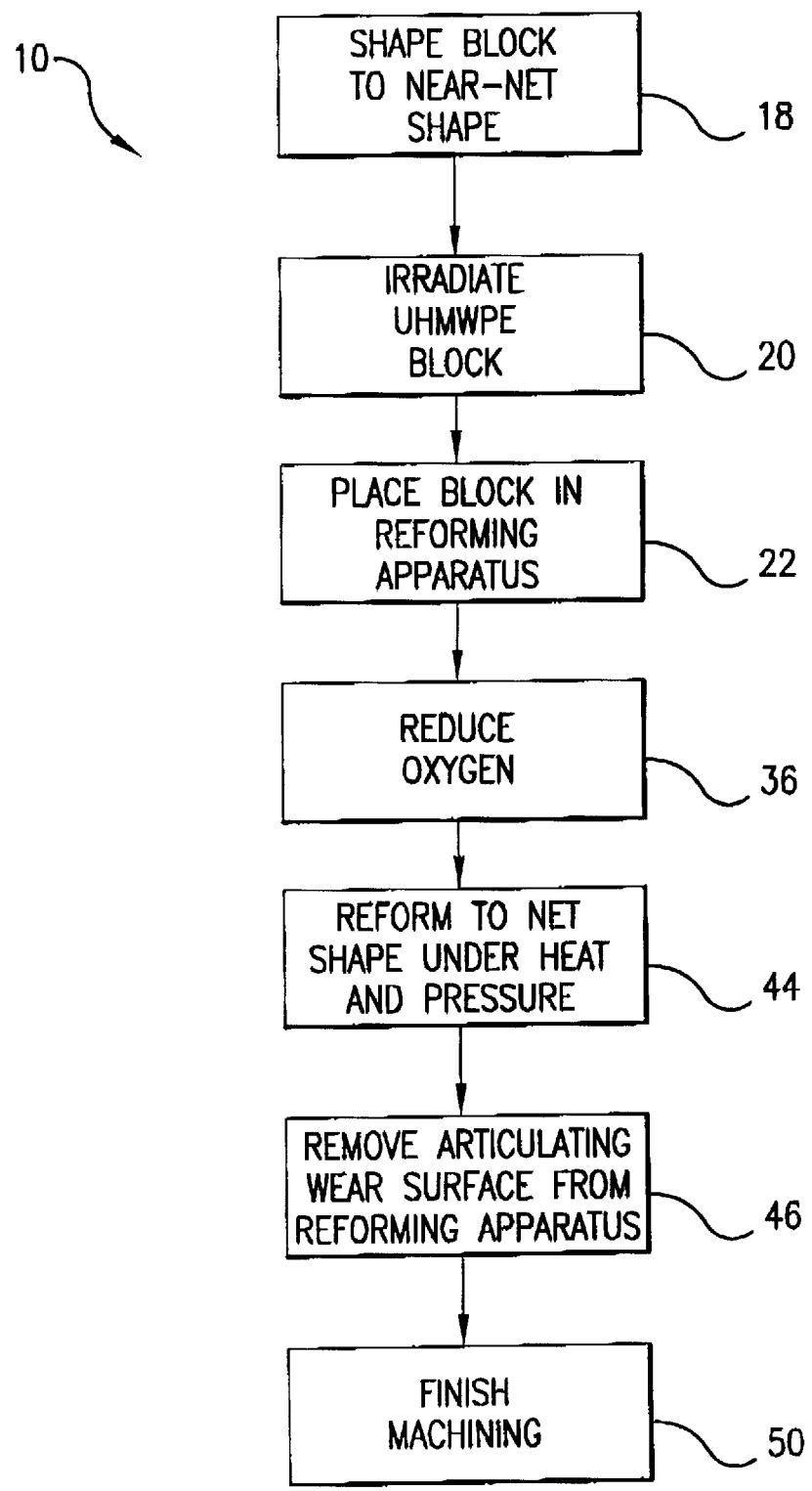
FIG. 1 is a flowchart illustrating an embodiment of the method of manufacture of an articulating bearing surface of the present invention.
Figure 2:
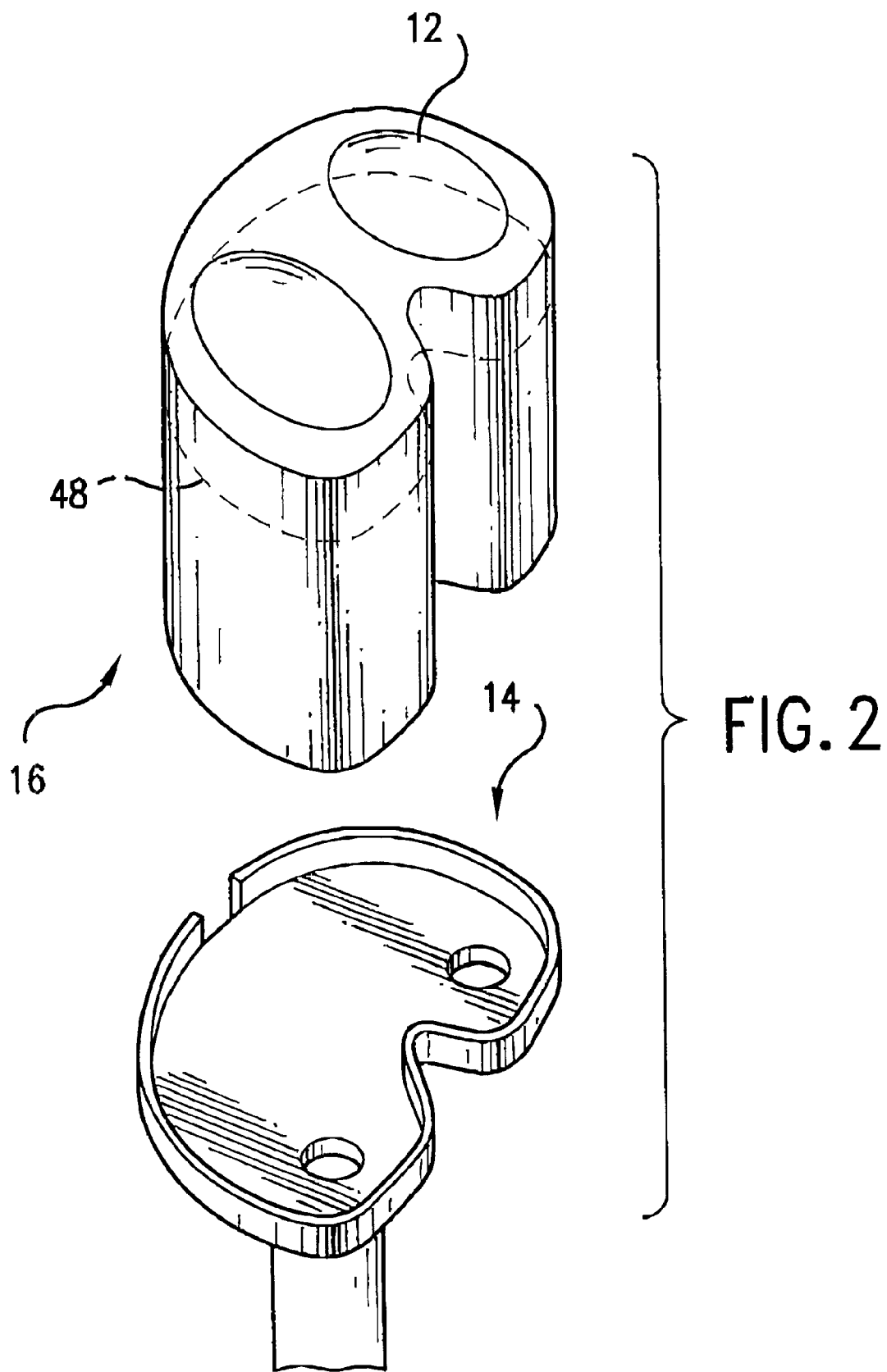
FIG. 2 is a perspective view of an embodiment of a near-net shape articulating bearing surface of the present invention, shown in association with a tibial tray.
Figure 3:
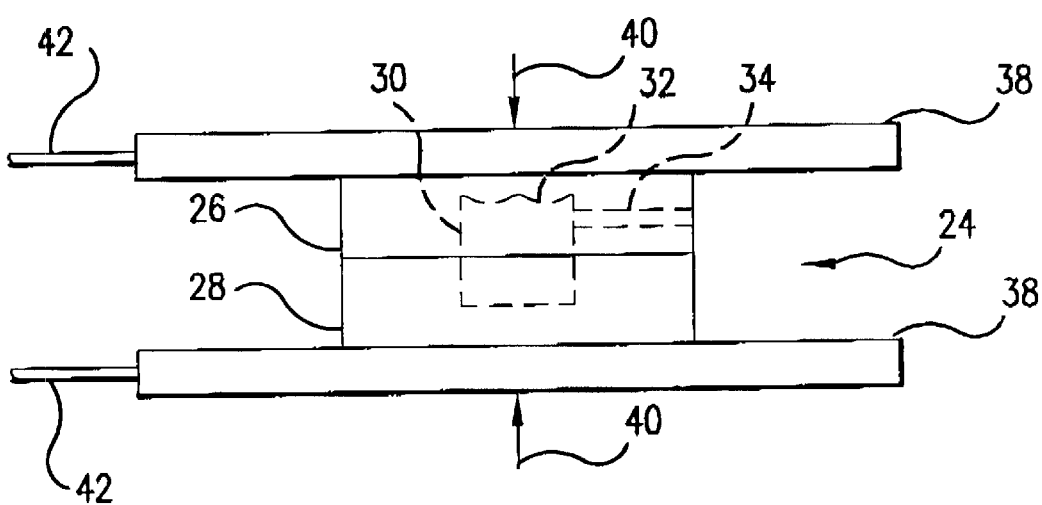
FIG. 3 is a plan view of a compression mold and heated platen assembly used in the method shown in FIG. 1.

Referring now to the drawings, and more particularly to FIG. 1, there is shown an embodiment of a flowchart illustrating a method 10 of manufacturing an articulating bearing surface 12 (FIG. 2) for use in an orthopaedic implant, such as a tibial knee implant 14.

Method of manufacture 10 of articulating bearing surface 12 begins with the step of shaping a block 16 of UHMWPE to a near-net shape (block 18). More particularly, block 16 is shaped using known machining processes such that the peripheral side edges of block 16 substantially conform to the general desired shape of block 16 when in a completed state. The general contour of articulating bearing surface 12 formed in block 16 may be substantially shaped, or may be left generally flat, depending upon the amount of physical deformation of articulating bearing surface 12 during the method 10 of the present invention. In the embodiment shown, block 16 is shaped with an approximate contour of a net shaped articulating bearing surface.

Near-net shaped block 16 is then irradiated with a sufficient amount of radiation energy to crosslink at least a portion of the UHMWPE (block 20). Preferably the net shaped block is irradiated in a low oxygen environment to prevent oxidation during the irradiation step and is kept in a low oxygen environment until the reforming step. Alternatively, an oversize block can be irradiated and then machined to remove any oxidized outer layer prior to the reforming step. Depending upon the amount of radiation energy used during the crosslinking process, at least the UHMWPE adjacent to articulating bearing surface 12 is crosslinked to provide improved wear and abrasion resistance properties. The radiation energy preferably is in the form of electron beam radiation, but may also be in the form of gamma ray radiation, x-ray radiation, ultraviolet radiation, neutron particle beam radiation, or proton particle beam radiation. In the embodiment shown, the UHMWPE of block 16 is crosslinked using a 10 MeV electron beam providing a total radiation dose level of between approximately 25 and 500 kGy, preferably between 100 and 250 kGy, and more preferably between 140 and 180 kGy. The amount of penetration of the radiation may be varied to provide different physical properties. A lower power radiation source may be used to provide lesser penetration, or portions of block 16 may be shielded to reduce penetration. Portions of block 16 with a higher radiation dose will have a higher wear and abrasion resistance, while other portions of block 16 with a lower radiation dose will have a higher tensile strength, impact strength, and fracture toughness.

After block 16 is crosslinked using radiation energy, block 16 is then placed within a reforming apparatus having a complementary bearing surface against which block 16 is pressed to form the articulating bearing surface used in the orthopaedic implant 14 (block 22). In the embodiment shown, the reforming apparatus is in the form of a compression mold 24 having two mold halves 26 and 28 which define a mold cavity 30 therebetween. The mold cavity 30 defined by mold half 26 includes the complimentary articulating bearing surface 32 against which block 16 is pressed to define the articulating bearing surface 12.

Block 16 is placed with the near-net shaped articulating bearing surface 12 adjacent to complimentary articulating bearing surface 32 within mold cavity 30. Mold halves 26 and 28 are then assembled together and the amount of oxygen within mold cavity 30 is reduced (block 36). Reducing the amount of oxygen within mold cavity 30 during the manufacturing process inhibits oxidation of the UHMWPE during subsequent heating and pressing steps, as will be described hereinafter. The oxygen within mold cavity 30 may be reduced by applying a vacuum pressure to mold cavity 30 using a vacuum source (not shown) attached to a port 34 disposed in communication with mold cavity 30. Alternatively, an inert gas such as nitrogen or argon may be introduced into mold cavity 30 through port 34.

Compression mold 24 is placed between a pair of platens 38 which provide the dual functionality of pressing mold halves 26 and 28 together (indicated by lines 40), as well as heating mold halves 26 and 28 through heat transfer primarily via conduction (block 44). Each platen 38 includes an integral heater (not shown) which is connected to a source of electrical power, such as through electrical conductors 42.

Block 16 is simultaneously pressed and heated so that block 16 is reformed with a net shape articulating bearing surface (block 44). During the reforming process, preferably the block is heated above the melting point of UHMWPE. Heating of the UHMWPE above its melting point allows free radicals in the UHMWPE formed during the crosslinking step to react with other free radicals in the UHMWPE, thereby forming a stable bond. The amount of time required during the reforming process to form the net shaped articulating bearing surface 12 and to allow reduction in free radicals in the UHMWPE is of course dependent upon the temperature at which the reforming process occurs. The amount of time required during the reforming process may take from a few minutes to several hours, depending upon whether the temperature of the UHMWPE is raised substantially above the melting point thereof, or is maintained at or slightly below the melting point thereof.

After the net shaped articulating bearing surface 12 is formed in block 16 within compression mold 24, block 16 is cooled and removed from within compression mold 24 (block 46). A portion of block 16 is then machined using any suitable machining process to allow block 16 to mate with tibial knee implant 14. For example, the portion of block 16 on a side of phantom line 48 generally opposite from articulating bearing surface 12 may be shaped and/or removed using suitable machining processes to allow block 16 to mate with tibial knee implant 14. Of course, block 16 may be machined to define suitable keying and/or interlocking structures for interconnection with tibial knee implant 14 (block 50).

In the embodiment shown, block 16 is reformed under heat and pressure using compression mold 24 and heated platens 38. However, other suitable reforming methods may be used which apply heat and pressure, such as isostatic forming techniques, stamping, thermoforming, etc.

The method of the present invention of forming an articulating bearing surface for use in an orthopaedic implant provides an articulating bearing surface with improved physical properties. By limiting the penetration depth of the radiation energy which is used during crosslinking, the UHMWPE which defines the articulating bearing surface is provided with improved wear and abrasion resistance properties, and the portion of block 16 which receives lower doses of radiation energy has other higher physical properties such as tensile strength, impact strength, and fracture toughness. The reforming of block 16 under heat and pressure to define the molded, net shaped articulating bearing surface 12 provides articulating bearing surface 12 with an improved surface finish when compared with machined articulating bearing surfaces. The improved smoothness of net shaped articulating bearing surface 12 reduces friction during use within a patient.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of manufacturing an articulating bearing surface for use in an orthopaedic implant, comprising the steps of:

provided a block of ultra-high molecular weight polyethylene;

shaping said block with a near-net shape articulating bearing surface;

irradiating said block with sufficient radiation energy to crosslink at least a portion of said ultra-high molecular weight polyethylene;

placing said irradiated block within a reforming apparatus having a complimentary articulating bearing surface; and reforming said block by heating said block and pressing said block against said complimentary articulating bearing surface, thereby reforming said articulating bearing surface.

2. The method of claim 1, comprising the further steps of:

removing said block from said reforming apparatus; and machining a portion of said block other than said articulating bearing surface whereby said block mates with said orthopaedic implant.

3. The method of claim 1, comprising the further step of reducing the amount of oxygen within said reforming apparatus prior to said reforming step.

4. The method of claim 3, wherein said step of reducing the amount of oxygen within said reforming apparatus comprises one of:

applying a vacuum pressure within said reforming apparatus; and introducing an inert gas within said reforming apparatus.

5. The method of claim 1, wherein said block is heated to a temperature allowing free radicals in said crosslinked ultra-high molecular weight polyethylene to react together and form stable bonds with each other.

6. The method of claim 5, wherein said block is heated above the melting point of said ultra-high molecular weight polyethylene.

7. The method of claim 1, wherein said reforming apparatus comprises a compression mold.

8. The method of claim 7, wherein said compression mold includes two mold halves defining a mold cavity therebetween, said irradiated block is placed within said mold cavity, and said reforming apparatus further comprises a pair of heated platens for pressing said mold halves together and heating said mold halves.

9. The method of claim 1, wherein said articulating bearing surface of said block is provided with a higher dose of radiation energy than another portion of said block.

10. The method of claim 1, wherein said shaping step occurs after said irradiating step.

11. The method of claim 1, wherein said reforming step provides said block with a net shape articulating bearing surface.

12. The method of claim 1, wherein said radiation energy consists of one of gamma rays, x-rays, ultraviolet radiation, neutron particle beam, proton particle beam, and electron particle beam.

13. The method of claim 1, wherein said articulating bearing surface is configured for use with a tibial knee implant.

14. A method of manufacturing an articulating bearing surface for use in an orthopaedic implant, comprising the steps of:

provforming a block of ultra-high molecular weight polyethylene;

irradiating said block with sufficient radiation energy to crosslink at least a portion of said ultra-high molecular weight polyethylene;

placing said irradiated block within a reforming apparatus having a complimentary articulating bearing surface; and reforming said block by heating said block to a temperature allowing free radicals in said crosslinked ultra-high molecular weight polyethylene to react together and form stable bonds with each other and pressing said block against said complimentary articulating bearing surface, thereby reforming said articulating bearing surface.

* * * * *